United States Patent
Endl et al.

(10) Patent No.: US 7,064,190 B1
(45) Date of Patent: Jun. 20, 2006

(54) ANTIGEN-SPECIFIC, ACTIVATED T LYMPHOCYTES, DETECTION AND USE

(75) Inventors: Josef Endl, Weilheim (DE); Peter Stahl, Bernried (DE); Winfried Albert, Eberfing (DE); Guenther-Gerhard Jung, Tübingen (DE); Dolores J. Schendel, München (DE); Edgar Meinl, Krailling (DE); Klaus Dornmair, Emmering (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/441,061

(22) Filed: Nov. 16, 1999

Related U.S. Application Data

(60) Division of application No. 09/343,406, filed on Jun. 30, 1999, now abandoned, which is a continuation of application No. 08/967,242, filed on Nov. 5, 1997, now abandoned, which is a continuation of application No. 08/374,468, filed on Jan. 18, 1995, now abandoned.

(30) Foreign Application Priority Data

| Jan. 20, 1994 | (DE) | ................................. P44 01 629 |
| Feb. 4, 1994 | (DE) | ................................. P44 03 522 |
| May 24, 1994 | (DE) | ................................. P44 18 091 |

(51) Int. Cl.
*C07K 14/74* (2006.01)
*C07K 16/00* (2006.01)

(52) U.S. Cl. ...................... 530/402; 530/325; 530/326; 530/327; 530/328; 530/403

(58) Field of Classification Search ............. 424/185.1, 424/192.1, 193.1, 810; 514/2, 12, 13, 14, 514/15; 530/300, 324, 325, 326, 327, 328, 530/402, 403
See application file for complete search history.

(56) References Cited

U.S. PATENT DOCUMENTS 5,489,742 A * 2/1996 Hammer et al.

FOREIGN PATENT DOCUMENTS

| EP | 0 519 469 | 12/1992 |
| WO | WO 89/12459 | 12/1989 |
| WO | WO 92/05446 | 4/1992 |
| WO | WO 92/20811 | 11/1992 |
| WO | WO 94/12529 | 6/1994 |

OTHER PUBLICATIONS

Ramensee et al (Immunogenetics (1995) 41:178-228).*
Li et al., *J. Immunol.*, 152(2), 930-934, pp. 1994, "Identification of Autoantibody Epitopes of Glutamic Acid Decarboxylase in Stiff-ManSyndrom Patients".
Harrison et al., *J. Clin Invest.*, 89, Apr. 1992, pp. 1161-1165, "Isletreactive T cells are a marker of preclinical insulin-dependent Diabetes".
Christie et al., *Diabetes*, 41, Jul. 1992, pp. 782-787, "Antibodies to GAD and Tryptic Fragments of Islet 64k Antigen as Distinct Markers for Development of IDDM".
"Glutamic Acid Decarboxylase 67-reactive T Cells: A Marker of Insulin dependent Diabetes"; Margo C. Honeyman et al., J. Exp. Med. vol. 177 Feb. 1993; pp. 535-540.
"Glutamic Acid Decarboxylase Autoantibodies in Preclinical Insulin dependent Diabetes"; Henry J. De Aizpurua, et al., Proc. Natl. Acad. Sci. USA; vol. 89; Oct. 1992; Medical Sciences; pp. 9841-9845.
"Two Human Glutamate Decarboxylases, 65-kDa GAD and 67-kDa GAD, Are each Encoded By A Single Gene"; Ding-Fang Bu et al.; Proc. Natl.. Acad. Sci. USA; vol. 89; Mar. 1992; Medical Sciences; pp. 2115-2119.
Engelhard, V.H., Curr. Opin. Immunol. 6:13-23, 1994. Structure of peptides associated with MHC Class 1 molecules.
Mauch, L. et al., Eur. J. Biochem. 212:597-603, 1993. Characterization of a linear epitope within the human pnacreatice 64-kDa glutamic acid decarboxylase and its autoimmune recognition by sera from insulin-dependent diabetes melitus patients.
Smilek, D. et al., P.N.A.S. 88:9633-9637, 1991. A single amino acid change in a myelin basis protein peptide confers the capacity to prevent rather than induce experimental autoimmune encephalomyelitis.

* cited by examiner

*Primary Examiner*—Christina Chan
*Assistant Examiner*—F. Pierre VanderVegt
(74) *Attorney, Agent, or Firm*—Rothwell, Figg, Ernst & Manbeck pc

(57) ABSTRACT

The invention concerns autoreactive peptides, peptide-MHC complexes, T cell subpopulations that react thereto as well as diagnostic and therapeutic applications of these compounds.

17 Claims, 6 Drawing Sheets

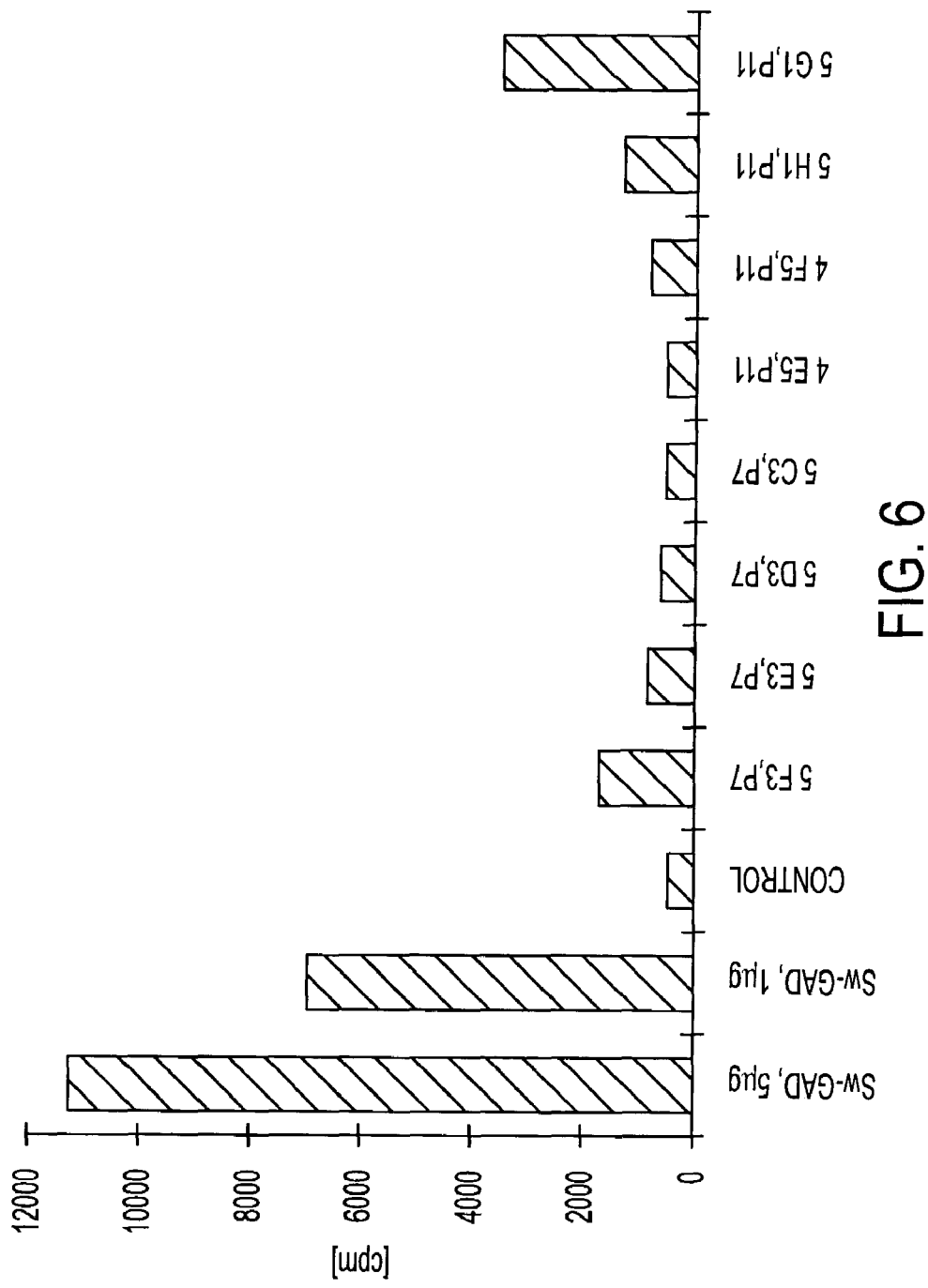

ANTIGEN-SPECIFIC, ACTIVATED T LYMPHOCYTES, DETECTION AND USE

CROSS REFERENCE TO RELATED APPLICATION

This application is a divisional of application Ser. No. 09/343,406, filed Jun. 30, 1999 now abandoned, which is a continuation of application Ser. No. 08/967,242, filed Nov. 5, 1997 (abandoned), which is a continuation of application Ser. No. 08/374,468, filed Jan. 18, 1995 (abandoned).

The present invention concerns peptides which cause an autoimmune reaction, complexes of these peptides with molecules of the major histocompatability complex (MHC), T cell subpopulations which react with the peptides or/and the complexes of peptides and MHC molecules as well as diagnostic and therapeutic uses of these compounds.

The elucidation of the molecular interrelations in the development of autoimmune diseases such as rheumatoid arthritis and juvenile diabetes (IDDM) has rapidly advanced in recent years and has meanwhile revealed concrete applications for early diagnosis and for a causal therapy of these diseases.

It is now certain that, in addition to a genetic disposition, environmental factors also play a role in the development of these diseases. For example in the case of IDDM, at the genetic risk factor level, only a few alleles of the MHC class II antigens are closely associated with this disease. Thus it is possible to define a risk group for IDDM by an analysis of these alleles (cf. e.g Thomson et al., Am. J. Hum. Genet. 43 (1988), 799–816 or Todd et al., Nature 329 (1987), 599–604).

The environmental factors involved in the development of IDDM are probably exogenic peptide sequences that act as an immunogen. Viral antigens have been discussed among others in this connection which have partial homologies to endogenous structures. Under particular circumstances, in particular in the postnatal phase, antigens taken up through the food such as bovine serum albumin can induce an immune response which can trigger an autoaggressive process due to homologies to endogenous structures.

The progressive destruction of the pancreatic β cells by cytotoxic lymphocytes is typical for the disease course in IDDM. This process starts a long time before there is a manifest disorder of glucose metabolism. Over 90% of the β cells are already destroyed when there is a detectable manifestation of diabetes. The early detection of these autoaggressive T cells in persons at risk would therefore be extremely important in order to provide a causal therapy for the affected individuals.

Nowadays it has been established that the destruction of endogenous tissues in autoimmune diseases progresses very slowly at first. In the initial stage of this process the autoaggressive T cells probably only recognize one or a few auto-antigens. The work of Kaufman et al (Nature 368 (1993), 69–72) and Tisch et al (Nature 368 (1993), 72–78) on an animal model (NOD mouse) of type I diabetes have shown that in the case of spontaneously occurring diabetes in this mouse strain the initial T cell-mediated autoimmune reaction is directed towards glutamic acid decarboxylase. In this case only 1 to 2 epitopes at the C terminus of glutamic acid decarboxylase (GAD) are recognized initially in the NOD mouse. At this time it is not yet possible—as set forth above—to determine any changes in glucose metabolism whereas a perinsulitis is already detectable. Only in the further course of the disease does the spectrum of GAD peptides recognized by the autoaggressive T cells expand.

After the diabetes becomes manifest, it is also possible to detect pre-activated T cells against other islet cell antigens e.g. peripherin, heat shock protein HSP 65 and carboxypeptidase H.

There is evidence that in the case of humans the immune response to GAD is also causally linked to the development of type I diabetes. Thus for example it is possible to detect auto-antibodies against GAD in over 80% of pre-diabetics, although however, the aetiological role of these auto-antibodies is judged to be of minor importance. On the contrary it is assumed that there is a progressive destruction of pancreatic β cells by T lymphocytes in type I diabetes. These T lymphocytes directed towards GAD have already been detected by several research groups (Harrison et al., J. Clin. Invest. 89 (1992), 1161; Honeyman et al., J. Exp. Med. 177 (1993), 535). The auto-antibodies found by these groups reacted with a peptide fragment composed of the amino acids 208 to 404 of the GAD 67 kd molecule.

Polypeptides from the human GAD 65 kd molecule which react autoimmunely are disclosed in EP-A-0 519 469. These polypeptides have the amino acid sequence:

X-P-E-V-K-(T or E)-K-Z, (SEQ ID NO:1)

in which X is an optional sequence selected from 1 to 10 amino acids and Z is an optional sequence selected from 1 to 8 amino acids.

An object of the present invention was to provide new auto-reactive peptides which react with T cells from type I diabetics, in particular with T cells from recently discovered type I diabetics and thus define early auto-epitopes.

This object is achieved by peptides, peptide derivatives or molecules which bind analogously which are suitable for the detection, isolation, proliferation, anergization or/and elimination of auto-reactive T cells. A subject matter of the invention is therefore a peptide or peptide derivative comprising:

(a) the amino acid sequence (I) G-M-A-A-L-P-R-L-I-A-F-T-S-E-H-S-H-F-S-L-K-K-G-A-A, (SEQ ID NO:2)
(b) the amino acid sequence (II) E-R-G-K-M-I-P-S-D-L-E-R-R-I-L-E-A-K-Q-K, (SEQ ID NO:3)
(c) one of the amino acid sequences shown in FIG. 1 or 2,
(d) partial regions of the amino acid sequences shown in (a), (b) or/and (c) with a length of at least 6 amino acids or/and
(e) amino acid sequences which have a specificity or/and affinity of binding to MHC molecules which is essentially equivalent to that of the amino acid sequences shown in (a), (b), (c) or/and (d).

A peptide or peptide derivative according to the invention preferably comprises (a) the amino acid sequence (I),
(b) the amino acid sequence (II),
(c) partial regions of the amino acid sequences (I) or/and (II) or/and
(d) amino acid sequences with an essentially equivalent specificity or/and affinity of binding to MHC molecules as the amino acid sequences from (a), (b) or/and (c).

A peptide or peptide derivative according to the invention preferably comprises the partial region

L-P-R-L-I-A-F-T-S-E-H-S-H-F(SEQ ID NO:4)

of the amino acid sequence (I) or a sequence derived therefrom in which the N-terminal sequence L-P and the C-terminal sequence H-F are conserved.

The amino acid sequence (I) corresponds to the amino acid residues 266–290 of the human GAD 65 and the amino acid sequence (II) corresponds to the amino acid sequence 306–325 of the human GAD 65. The amino acid sequences shown in FIGS. 1 and 2 are also partial sequences of human GAD 65.

Surprisingly it was found that peptides which correspond to the amino acid sequences 266 to 285 and 306 to 325 of the human GAD 65 specifically reacted with T cell subpopulations which were isolated from recently discovered type I diabetics. Therefore the peptides according to the invention are early auto-epitopes which can be used for a very early diagnosis of type I diabetes. Furthermore the peptides according to the invention can also be used therapeutically by inactivating the T cell population that reacts with the peptides.

Preferred examples of T cell subpopulations which react with the peptides according to the invention having amino acid sequences (I) and (II) are the T cell lines 6/7 and 6/10 or T cells with an equivalent binding specificity. The T cell lines 6/7 and 6/10 were deposited on the 10 May 1994 at the "Deutsche Sammlung von Mikroorganismen und Zellkulturen GmbH" (DSM), Mascheroder Weg 1b, 38124 Braunschweig, Germany under the numbers DSM ACC2172 (6/7) and DSM ACC2173 (6/10) according to the regulations of the Budapest Treaty.

The amino acid sequences (I) and (II) are partial regions of the 65 kd isoform of human glutamic acid decarboxylase (GAD), the complete amino acid sequence of which has been described by Bu et al (Proc. Natl. Acad. Sci. USA 89 (1992), 2115 ff). The amino acid sequences (I) and (II) were found by setting up T cell lines from the peripheral blood of type I diabetics and subsequent in vitro stimulation with GAD from pig brain and testing these T cell lines in a proliferation assay with synthetic peptide sequences which were derived from the human GAD sequence.

The peptides according to the invention can be produced by well-known synthesis processes using chemical methods or they can be produced by genetic engineering by cloning and expression of a DNA sequence coding for these peptides in a suitable host cell, in particular *E. coli*.

In addition the present invention also includes peptides with partial regions of the specifically stated amino acid sequences (I) or (II) or of the amino acid sequences shown in FIGS. 1 and 2 which have a length of at least 6 amino acids, preferably at least 8 amino acids, particularly preferably of at least 10 amino acids and most preferably of at least 15 amino acids.

The minimum length of a peptide according to the invention is determined by its capability to recognize a MHC molecule, to bind specifically to it and to react with the corresponding T cell receptor.

The maximum length of the sections in a peptide according to the invention that are derived from GAD and bind MHC is preferably 100 amino acids, particularly preferably 50 amino acids and most preferably 25 amino acids.

In addition to peptides having the amino acid sequences (I) and (II) or partial regions thereof, the invention also concerns peptides with amino acid sequences which exhibit an essentially equivalent specificity or/and affinity of binding to MHC molecules as the aforementioned sequences and which are preferably derived by substitution, deletion or insertion of individual amino acid residues or short sections of amino acid residues from the amino acid sequences (I) or (II) or alienated substances which bind analogously.

The present invention also particularly concerns peptide variants whose sequence does not completely correspond to the above-mentioned amino acid sequences but which have the same or closely related "anchor positions". In this connection the terms "anchor position" means an amino acid residue essential for binding to a MHC molecule in particular to a MHC molecule of classes DR3, DR4 or DQ. The anchor positions for the DRB10401 binding motive are for example given in Hammer et al., Cell 74 (1993), 197–203. Such anchor positions are conserved in peptides according to the invention or optionally replaced by amino acid residues with chemically very closely related side-chains (e.g. alanine by valine, leucine by isoleucine and vica versa). The anchor positions in the peptides according to the invention can be determined in a simple manner by testing variants of the above-mentioned specific peptides for their binding capability to MHC molecules. Peptides according to the invention are characterized in that they exhibit an essentially equivalent specificity or/and affinity of binding to MHC molecules as the aforementioned peptides. The peptides derived from peptides having the amino acid sequences (I) or (II) or from the amino acid sequences shown in FIGS. 1 and 2 preferably have a sequence homology of at least 30%, particularly preferably of at least 50% and most preferably of at least 60% to the parent peptides or partial sequences thereof.

Examples of variants of the specifically stated peptides are the corresponding homologous peptide sections from human GAD 67, the complete amino acid sequence of which has also been described by Bu et al., supra.

The term "essentially equivalent specificity or/and affinity of binding to MHC molecules" also includes an improved binding specificity or/and affinity compared to the amino acid sequences (I), (II) or the amino acid sequences shown in FIGS. 1 and 2 which is found particularly in the case of truncated peptides which have a length of preferably 8 to 15 amino acids.

Moreover the present invention also includes peptide derivatives. This term includes peptides in which one or several amino acids have been derivatized by a chemical reaction. Examples of peptide derivatives according to the invention are in particular those molecules in which the backbone or/and reactive amino acid side groups e.g free amino groups, free carboxyl groups or/and free hydroxyl groups have been derivatized. Specific examples of derivatives of amino groups are sulfonic acid or carboxylic acid amides, thiourethane derivatives and ammonium salts e.g. hydrochlorides. Examples of carboxyl group derivatives are salts, esters and amides. Examples for hydroxyl group derivatives are O-acyl or O-alkyl derivatives. Furthermore the term peptide derivative according to the present invention also includes those peptides in which one or several amino acids are replaced by naturally occurring or non-naturally occurring amino acid homologues of the 20 "standard" amino acids. Examples of such homologues are 4-hydroxyproline, 5-hydroxylysine, 3-methylhistidine, homoserine, ornithine, β-alanine and 4-aminobutyric acid.

Those peptides are particularly preferred which have an essentially equivalent specificity or/and affinity of binding to MHC molecules as peptides having the amino acid sequences (I) or (II) but which, in contrast to these peptides, do not cause an activation of T cells but rather the production of an anergic state in the T cells.

The present invention also covers polypeptides in which the MHC-binding peptide section is a component of a larger polypeptide unit in which the link between the MHC-binding peptide and the rest of the polypeptide unit preferably has a predetermined breaking point e.g. a protease cleavage site.

A futher subject matter of the present invention is a peptide or peptide derivative which carries a substance that generates a signal or a marker group e.g. a fluorescent marker group (e.g. rhodamine, phycoerythrin), digoxin, biotin, a radioactive group or a toxin group (e.g. ricin, cholera toxin etc.). Coupling of the peptide according to the invention to marker groups enables the peptide to be used as a diagnostic agent for in vivo or in vitro (e.g. imaging) applications or as a therapeutic agent. Furthermore the peptide according to the invention can also for example be present in a cyclised form or in an oligomeric form in which the sequences that are important for binding to the MHC molecule are separated from one another by spacer regions.

The invention also concerns peptide-mimetic substances which exhibit an essentially equivalent specificity or/and affinity of binding to MHC molecules as the aforementioned peptides or peptide derivatives. Peptide-mimetic substances or peptide-mimetics are compounds that can replace peptides with regard to their interaction with the MHC molecules and which can have an increased metabolic stability, improved bioavailability and longer duration of action compared to the native peptides. Methods for the production of peptide-mimetics are described by Giannis and Kolter, Angew. Chem. 105 (1993), 1303–1326, Lee et al., Bull. Chem. Soc. Jpn. 66 (1993), 2006–2010 and Dorsch et al., "Kontakte" (Darmstadt) (1993) (2), 48–56. Reference is made to the disclosure of these references with regard to the production of peptide-mimetic substances according to the invention.

The present invention in addition concerns a complex which comprises at least one peptide, peptide derivative or peptide-mimetic according to the invention and at least one MHC molecule or a peptide-binding derivative of a MHC molecule. In this complex a peptide, peptide derivative or peptide-mimetic with a binding constant of preferably at least $10^{-7}$ l/mol, particularly preferably in the range of $10^{-8}$–$10^{-9}$ l/mol, is bound to a MHC molecule or peptide-binding derivative of a MHC molecule. Alternatively the peptide, peptide derivative or peptide-mimetic can also be covalently coupled to the MHC molecule e.g. by means of a photolinker or as a covalent genetic peptide-MHC fusion. Such a peptide-MHC fusion protein preferably contains a HLA-DR beta chain and an autoreactive peptide that is genetically fused thereto. The complex particularly preferably contains a MHC class II molecule or a peptide-binding derivative thereof.

The MHC class II molecule is preferably of the DR type, for example of the DR1, DR2, DR3 or DR4 type. The MHC class II molecule is particularly preferably of the subtype DR B1 101, DR B1 0301, DR B1 0401, DR B1 0402, DR B1 0404 or DR B1 1601. The MHC class II molecule of subtype DR B1 0101 or DR B1 0401 is most preferred. The T cell line 6/7 (DSM ACC2172) proliferates with the autoreactive peptide of the amino acid sequence (I) in the presence of the DR B1 allele 0401 and 0101 or/and 1601. A proliferation in the presence of the DR B1 allele 0401 is found with the autoreactive peptide having the amino acid sequence (II). The T cell line 6/10 (DSM ACC2173) proliferates with the autoreactive peptides of the amino acid sequences (I) and (II) in the presence of the DR B1 allele 0401.

The nucleotide sequences for genes coding for a MHC class II molecule of the above subtypes are published in Corell et al. (Mol. Immunol. 28 (1991), 533–543). Reference is hereby made to these publications.

The term "peptide-binding derivative of a MHC molecule" comprises fragments of MHC molecules which are produced by proteolytic cleavage of native MHC molecules or by recombinant DNA techniques and which have essentially preserved their peptide-binding properties. In addition this term is also understood to include fusion proteins which also contain further polypeptide components in addition to a MHC part responsible for the peptide binding.

The peptide-MHC complexes according to the invention are preferably produced by association of peptide-free MHC molecules or MHC molecule derivatives with the peptides, peptide derivatives or peptide-mimetics according to the invention. The production of peptide-free MHC molecules can for example be carried out by unfolding native MHC molecules in order to dissociate bound peptides and refolding the empty MHC molecules (see Dornmair and McConnell, Proc. Natl. Acad. Sci. USA 87 (1990), 4134–4138 and WO91/14701).

On the other hand peptide-free MHC molecules can also be obtained by recombinant production of MHC molecules or derivatives thereof. Examples of this are the expression of MHC class II molecules in fibroblasts (Germain and Malissen, Ann. Rev. Immunol. 4 (1990), 281–315) as well as the expression of soluble MHC class II molecule derivatives without a membrane anchor in CHO cells (Wettstein et al., J. Exp. Med. 174 (1991), 219–228, Buelow et al., Eur. J. Immunol. 23 (1990), 69–76) and by means of the baculovirus expression system in insect cells (Stern and Wiley, Cell 68 (1992), 465–477; Scheirle et al., J. Immunol. 149 (1992), 1994–1999). MHC class I molecules have also been expressed in CHO cells (Fahnestock et al., Science 258 (1992), 1658–1662), in insect cells (Jackson et al., Proc. Natl. Acad. Sci. USA 89 (1992), 12117–12120; Matsamura et al., J. Biol. Chem. 267 (1992), 23589–23595) and in fibroblasts (Mage et al., Proc. Natl. Acad. Sci. USA 89 (1992), 10658–10661).

In addition it is also known that peptide-free MHC molecules can be expressed in E. coli (Parker et al., Mol. Immunol. 29 (1992), 371–378; Zhang et al., Proc. Natl. Acad. Sci. USA 89 (1992), 8403–8407; Garboczi et al., Proc. Natl. Acad. Sci. USA 89 (1992), 3429–3433; Altman et al., Proc. Natl. Acad. Sci. USA 90 (1993), 10330–10334). Reference is made for the present invention to the techniques for the recombinant expression of MHC molecules or MHC molecule derivatives described in these publications.

The MHC component of the complex according to the invention is preferably a recombinant MHC molecule or a peptide-binding derivative thereof and particularly preferably a soluble MHC molecule derivative in which the membrane anchor is partially or completely deleted.

In order to identify MHC molecules which present the autoreactive peptide according to the invention, the antigen-presenting cells of a donor are incubated with the peptide according to the invention in a labelled form and bound peptides are preferably firstly dissociated by denaturation of native MHC molecules. Subsequently the labelled MHC-peptide complexes can be immunoprecipitated with subtype specific antibodies which are directed towards framework-specific determinants of the MHC molecules and identified by the presence of the labelled peptides.

Alternatively EBV (Epstein-Barr virus) transformed B cells of the donor can be used as the antigen-presenting cells.

The production of the complexes according to the invention from a recombinant MHC molecule derivative can for example be carried out in such a way that DNA fragments for the soluble parts of the α and β chains of a MHC molecule, e.g. a MHC DR3, DR4 or DQ molecule, are isolated by PCR using cDNA from an EBV transformed B cell line of the donor as the template which expresses the corresponding MHC molecule. In this step it is preferable to introduce a purification aid, e.g. an oligohistidine segment (e.g. a hexahistidine segment), at the C terminus of the α and β chain by appropriate selection of the PCR primer. The PCR products can be subsequently subcloned in *E. coli* and expressed as inclusion bodies. The inclusion bodies can be solubilized by known methods (cf. references on the expression of MHC molecules in *E. coli*, supra) and the MHC proteins can be purified by means of metal chelate affinity chromatography. Subsequently the α and β subunits are renatured in the presence of the peptide.

The peptide-MHC complex according to the invention can also carry a marker group as described above in which case the marker group can be bound by known methods to the peptide component as well as to the MHC component of the complex.

A further subject matter of the present invention is an oligomerized peptide-MHC complex which contains at least two MHC molecules or MHC molecule derivatives that are associated by means of covalent or non-covalent interactions. An advantage of such an oligomerized peptide-MHC molecule complex compared to known monomeric complexes (with regard to the MHC molecule) is that it has a higher affinity and thus an improved diagnostic or/and therapeutic efficacy.

In one embodiment of the present invention such an oligomerized complex can be produced according to known methods by covalent cross-linking of monomeric peptide-MHC complexes via chemical coupling reagents e.g. N-succinimidyl-3(2-pyridylthio)propionate, 3-maleimido-benzoyl-N-hydroxysuccinimide ester, maleimidohexanoyl-N-hydroxysuccinimide ester, bis(maleimidomethyl)ether, disuccinimidyl suberate, glutardialdehyde etc. Optionally it is also possible to modify individual amino acids of the peptide component or the MHC component in such a way that special coupling reagents preferably attack at this position. Thus coupling by SH linkers or via amino groups can be achieved by introducing additional cysteine or lysine residues by recombinant means in the case of the protein component or by chemical synthesis in the case of the peptide component.

In a further embodiment of the present invention the oligomerized peptide-MHC complex can be produced in such a way that the peptide component binding to the MHC molecule is used as an oligomer i.e. as a peptide molecule that contains at least 2 MHC-binding regions in which the sequences that are important for binding to the MHC molecule are separated from one another by spacer regions. These spacer regions are usually comprised of 10–15 amino acids. Small hydrophilic amino acids such as glycine, alanine, serine, proline or combinations thereof are used. When peptide-free MHC molecules are renatured in the presence of these peptide oligomers the oligomerized complex according to the invention is formed which contains MHC molecules cross-linked by the oligomerized peptide components via non-covalent interactions.

In addition oligomerized peptide-MHC complexes can be produced by modifying recombinantly produced MHC molecules. Thus during the construction of vectors for the expression of recombinant α or β chains of MHC class II molecules it is possible to clone in a gene segment, preferably at the C-terminus, which codes for an epitope that is recognized by an antibody. This antibody can be of the IgG type but preferably of the IgM type. The renatured monomeric peptide-MHC complexes are then incubated with an antibody that recognizes the introduced epitope so that non-covalently cross-linked immune complexes composed of several antibodies and several peptide-MHC complexes are produced. The introduction of DNA segments that code for an epitope into the DNA fragments coding for the α or β chain of the MHC molecule can be achieved by means of well-known molecular biological techniques e.g. by insertion into restriction sites or by site-directed mutagenesis.

The oligomerized peptide-MHC complex according to the invention preferably contains a peptide which comprises the amino acid sequences (I), (II), the amino acid sequences shown in FIGS. 1 and 2, partial regions thereof or/and amino acid sequences derived therefrom, or a peptide derivative or peptide-mimetic thereof. The oligomerized complex can be preferably used as a diagnostic or therapeutic reagent in type I diabetes.

The invention therefore also concerns a pharmaceutical composition containing a peptide, peptide derivative, peptide-mimetic or/and a peptide-MHC complex as the active component, if desired, in combination with common pharmaceutical additives. The composition can in addition contain an accessory stimulating component e.g. cytokines such as IL-2 and IL-4 or/and the surface antigen B7 (Wyss-Coray et al., Eur. J. Immunol. 23 (1993), 2175–2180; Freeman et al., Science 262 (1993), 909–911) which can bind to the surface molecule CD-28 on a T cell. The presence of the accessory stimulating component can improve or/and modify the therapeutic effect of the composition.

Furthermore the present invention concerns the use of a pharmaceutical composition which contains a peptide, peptide derivative, peptide-mimetic or/and a peptide-MHC complex for the production of an agent for the diagnosis of diseases or of a predisposition to diseases that influence the immune system or for the diagnosis of tumour diseases or of a predisposition to tumour diseases, in particular for the diagnosis of autoimmune diseases or of a predisposition to autoimmune diseases, e.g. diabetes type I or type II, preferably diabetes type I.

Analogous diagnostic applications are, however, also possible in the case of other autoimmune diseases. Examples of such autoimmune diseases are multiple sclerosis where reactive T cells against the myelin basic protein or the proteolipid protein can be determined, rheumatoid arthritis where reactive T cells against collagen type II, cytokeratins and Hsp 65 can be determined, Basedow disease where reactive T cells against thyroid peroxidase can be determined.

In general a diagnostic application is possible for all diseases that influence the immune system such as e.g. also in the case of arteriosclerosis. In this case the disease has been shown to be associated with an immune response against the heat shock protein Hsp 65 (Xu et al., Lancet 341, 8840 (1993), 255–259).

A further application is the diagnostic detection of T cells which react to tumour antigens. Examples of this are T cells against a melanoma-associated antigen MAGE 1 which has been isolated from melanoma patients (van der Bruggen et al., Science 254 (1991), 1643–1647). The oligomerized complexes according to the invention can be used to detect these T cells at a stage in which the tumour is not yet detectable by conventional methods due to an inadequate cell mass. Moreover the detection of specifically reacting T cells can also be used to monitor an anti-tumour vaccination.

The present invention therefore also concerns a method for the determination of a specific T cell subpopulation which is characterized in that a sample containing T cells, which is preferably derived from a body fluid e.g. whole blood, is brought into contact with a peptide, peptide derivative, peptide-mimetic according to the invention or/and a complex according to the invention and the reaction of T cells with the peptide or complex is determined. A specific reaction of T cells with the complex or the peptide can for example be detected by an increased T cell proliferation which can for example be measured by the incorporation of radioactivity. On the other hand the reaction of T cells can also be determined directly by the use of a labelled peptide or complex. In this embodiment the peptide or the complex are preferably used with a fluorescent marker group coupled thereto. The evaluation can for example be carried out by FACS analysis in which the T cells are brought into contact with a first fluorescent marker that is coupled to a T cell-specific antibody and then with the peptide-MHC complex that is coupled to a second fluorescent marker and the presence of double labelled cells is determined by fluorographic analysis. In this way a T cell subpopulation is determined which is characterized by its reactivity with a peptide or peptide derivative according to the invention or/and with a peptide-MHC complex according to the invention. Due to the low concentration of the specific T cell population in blood, a selection for pre-activated T cells is preferably carried out as the first step of the method e.g. a selective concentration of IL-2 receptor-positive T cells by incubation with IL-2 or/and by incubation with IL-2 receptor antibodies and subsequent separation of the antibody-binding cells by using immunomagnetic methods for example. On the other hand the selection for pre-activated cells can be carried out after contact of the T cells with the peptide or the complex.

In a modification of the method the ratio of the pre-activated autoreactive T cells, i.e. T cells with the IL-2 receptor as the surface marker, to non-activated autoreactive T cells, i.e. T cells without the IL-2 receptor, can also be determined.

This method can be used in particular to diagnose type I diabetes and also for other diseases that influence the immune system or for the diagnosis of a predisposition to such diseases.

The present invention in addition concerns the use of a pharmaceutical composition which contains a peptide, peptide derivative, peptide-mimetic or/and a peptide-MHC complex according to the invention for the production of an agent for the therapy or prevention of diseases that influence the immune system. For the therapeutic application of the peptides according to the invention and the peptide-MHC complexes according to the invention, it is possible for example to use peptides or peptide-MHC complexes coupled to toxins, on the other hand it is also possible to use peptides alone or as components of the complex which, although enabling binding to the T cell receptor, do not cause activation of T cells i.e. have an anergizing effect.

The therapeutic action of such anergizing peptide analogues is due to the fact that the T cell receptor (TCR) must interact with a peptide which is presented by a MHC antigen of class I or class II in order to activate the T cells. In this process amino acids at the anchor positions of the peptide are particularly responsible for binding to the MHC molecule whereas other amino acids in the peptide contribute to the interaction with the TCR and thus cause a T cell stimulation. Thus it is possible to produce peptide analogues by amino acid substitutions in the peptides which still bind to the MHC molecule due to the presence of the anchor positions but on the other hand only cause a partial or no T cell activation (cf. e.g. Sloan-Lancaster et al., Nature 363 (1993), 156–159). Such peptide analogues can for example have the effect that the expression of particular surface molecules is set to a higher level (e.g. IL-2 receptor, LFA-1) but that no proliferation or cytokine expression takes place. T cells which interact with such a peptide analogue are transformed into a so-called anergic state i.e. they can no longer proliferate even after a subsequent regular stimulation with an immunogenic peptide. This anergic state lasts at least 7 days and can therefore be utilized therapeutically in the treatment of an autoimmune disease.

A further therapeutic aspect of the present invention is that the peptide or the complex of peptide and MHC molecule can be used as an antigen. Such an antigen can act in this case as an immunogen i.e. as an agent stimulating an immune response or as a tolerogen i.e. as an agent which causes an immune tolerance. The application as an immunogen can for example be used for vaccination against tumour antigend. Instead of the whole tumour cells hitherto used for this purpose it is possible to inject tumour-specific peptides recognized by the T cells in a complex with the corresponding MHC molecules in particular in the form of an oligomerized complex in order to produce a T cell response against the tumour. In order to increase the immune stimulation it is also possible to administer the complex in combination with additional stimulating substances. Cytokines such as IL2 or IL4 are for example suitable for this purpose which are optionally and preferably covalently linked to the peptide-MHC complex according to the invention. A further possibility is to associate the complex with accessory components for T cell activation in particular with essential surface molecules for antigen presenting cells e.g. the surface molecule B7.

A preferred therapeutic formulation is the incorporation of MHC molecules loaded with peptides into artificial vesicles e.g. lipid vesicles which can optionally carry further membrane-bound molecules such as e.g. B7 or/and immobilized cytokines.

The present invention in addition concerns the isolation of T cell subpopulations that react with a peptide or peptide-MHC complex according to the invention. In such a method a sample containing T cells which is for example derived from a body fluid that has previously been collected from a patient, is contacted with a peptide according to the invention or with a peptide-MHC complex according to the invention, the T cells that react with the peptide or complex are identified and if desired they are separated from other T cells. Also in this case it is possible to select for pre-activated T cells, i.e. T cells with the IL-2 receptor, before or/and after contact of the T cells with the peptide or the complex.

In such a method the peptide or peptide-MHC complex can be used in an immobilized form on a carrier which simplifies the separation of the positively reacting T cell population from other T cells. T cell lines can be set up by restimulation from the T cell subpopulations isolated in this manner. These autoreactive T cell lines can then be used to immunize patients.

A specific immunotherapy of type I diabetes comprises firstly isolating specific T cell lines against an autoantigen e.g. GAD 65 from IDDM patients. Then the fine specificity of the T cell lines is determined i.e. the autoreactive peptides are identified. Those T cell lines are selected for the later vaccination of the patients which recognize a predominant peptide i.e. a peptide to which several of the isolated T cell lines react. These are in particular T cell lines which recognize a peptide with the amino acid sequences (I) or (II).

If there is no clearly predominant peptide in a patient, several T cell lines have to be mixed for the later inoculation. The selected T cell clones are stimulated again before inoculation with antigen-presenting cells and with the appropriate peptides in order to ensure a good expression of activation molecules and in particular of the T cell receptors. Then the T cell lines are inactivated e.g. by heat treatment or/and radioactive irradiation preferably with a dose in the range of 4000–10000 rad, particularly preferably ca. 8000 rad and injected subcutaneously into the patient from which they were obtained using a cell number of preferably $10^7$ to $5 \times 10^7$. Usually at least three injections are spread over a time period of 6 to 12 months.

Subsequently the T cell response of the patient to the inoculate can be tested. For this the peripheral blood lymphocytes (PBLs) of the patient are isolated e.g. by means of Ficoll density gradient centrifugation and the proliferation caused by the inoculate is tested in a standard proliferation test. After a successful immunization it should be possible to detect a substantial proliferation of the patient's PBLs in response to the inoculate. A further control of the success of immunization is to determine the frequencies of the GAD-reactive T cells of the patient during the course of the immunization. This can for example be carried out by the standard method of limiting dilution using autologous stimulator cells which have been irradiated with e.g. 4000 rad after incubation with GAD. If the immunization proceeds successfully, the frequency of autoreactive T cells significantly decreases.

After the surface structures on the T cells of the inoculate that are recognized by the regulatory T cells have been narrowed down further, it is also possible to immunize with partial structures of the regulatory T cells e.g. with segments of the T cell receptor.

On the other hand T cells capable of division can be reinjected in the case of an anti-tumour vaccination which can lead to an active immunization of the patient against tumour cells.

In diagnostic and therapeutic methods for identifying or activating/inhibiting specific T cell subpopulations, an anti-idiotypic antibody which simulates the action of the MHC-peptide complex can also be used instead of the peptides or peptide-MHC molecules according to the invention. Such antibodies can be easily obtained by using a specific T cell subpopulation against a particular peptide as an immunogen for producing an antibody (e.g. in a mouse) or by firstly producing a first antibody against the MHC-peptide complex and then producing an anti-idiotypic antibody against the first antibody.

Therefore a subject matter of the present invention is also an antibody (first antibody) against a peptide or peptide derivative according to the invention or against a complex according to the invention which is obtainable by immunizing with the peptide, peptide derivative or complex and isolating an antibody produced by the immunization, preferably a monoclonal antibody produced by the method of Köhler and Milstein or further developments thereof.

Finally the invention also concerns an anti-idiotypic antibody against the first antibody obtainable by immunizing with the first antibody which is directed towards the peptide or peptide derivative or complex and isolating an anti-idiotypic antibody produced by the immunization.

Yet a further subject matter of the present invention is a T cell which reacts with an autoreactive peptide, peptide derivative or peptide-mimetic according to the invention or a complex of the peptide and MHC molecule. Preferred examples are T cells that are derived from the T cell lines 6/7 (DSM ACC2172) or 6/10 (DSM ACC2173) or which have an equivalent T cell receptor binding specificity i.e. recognize a peptide presented by a MHC molecule or peptide derivative having the amino acid sequences (I) or/and (II) or/and partial regions of these amino acid sequences.

It is intended to further elucidate the invention by the following examples in conjunction with FIGS. 1 to 4.

FIG. 1 shows autoreactive amino acid sequences (SEQ ID NO:19–22) according to the invention.

FIG. 2 shows further autoreactive amino acid sequences (SEQ ID NO:23–39) according to the invention.

Figure 3:
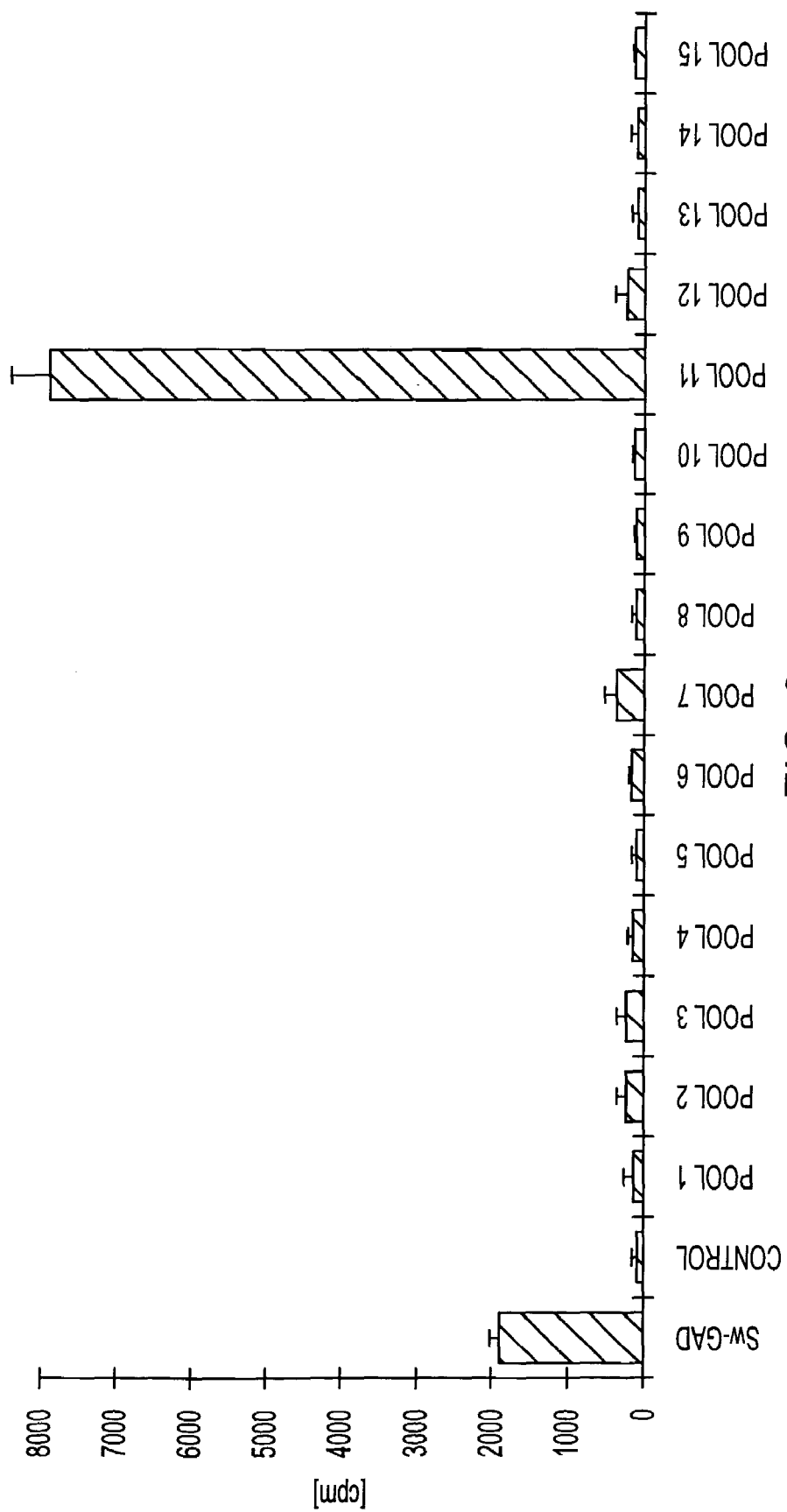
Figure 4:
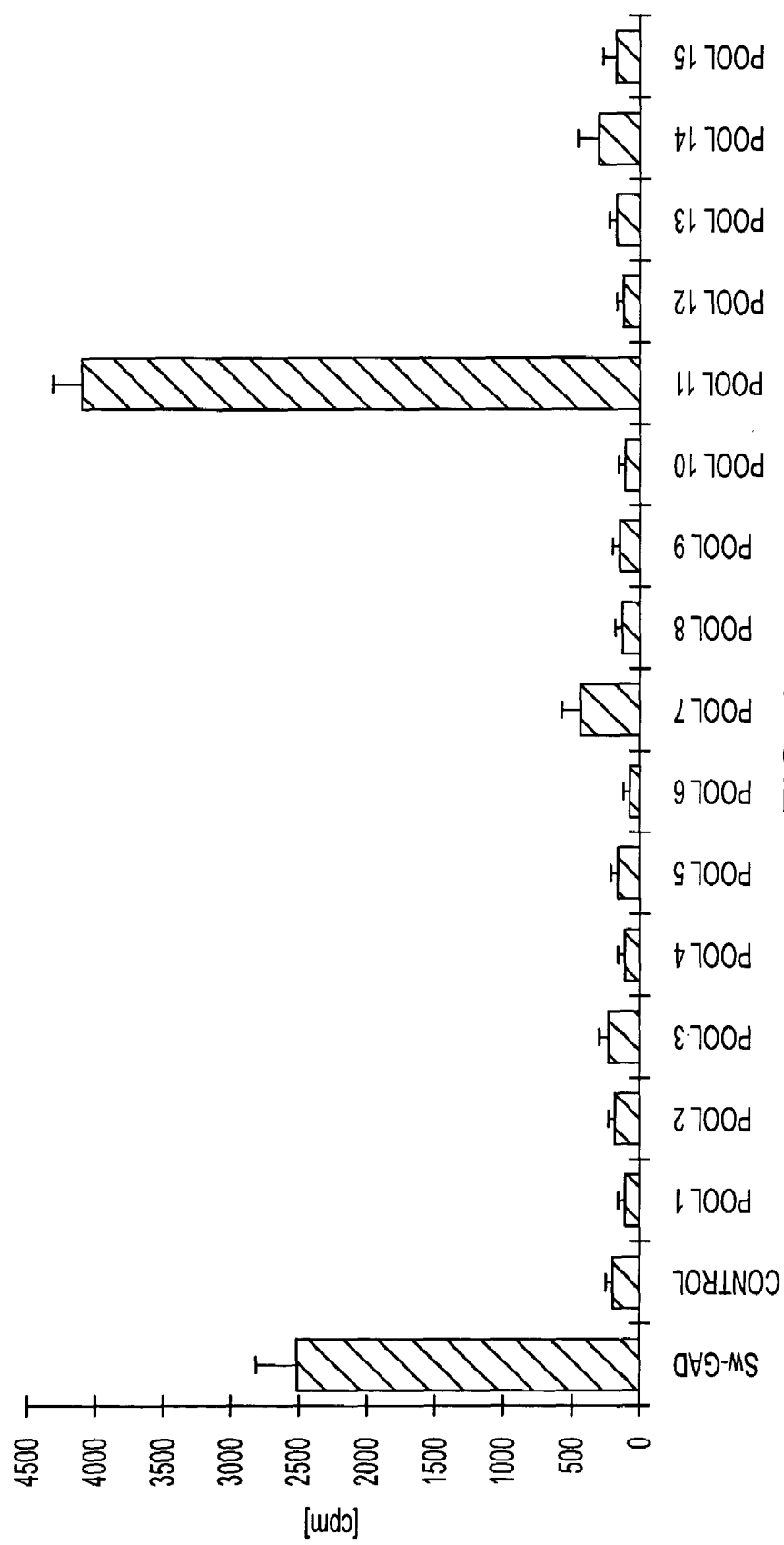
Figure 5:
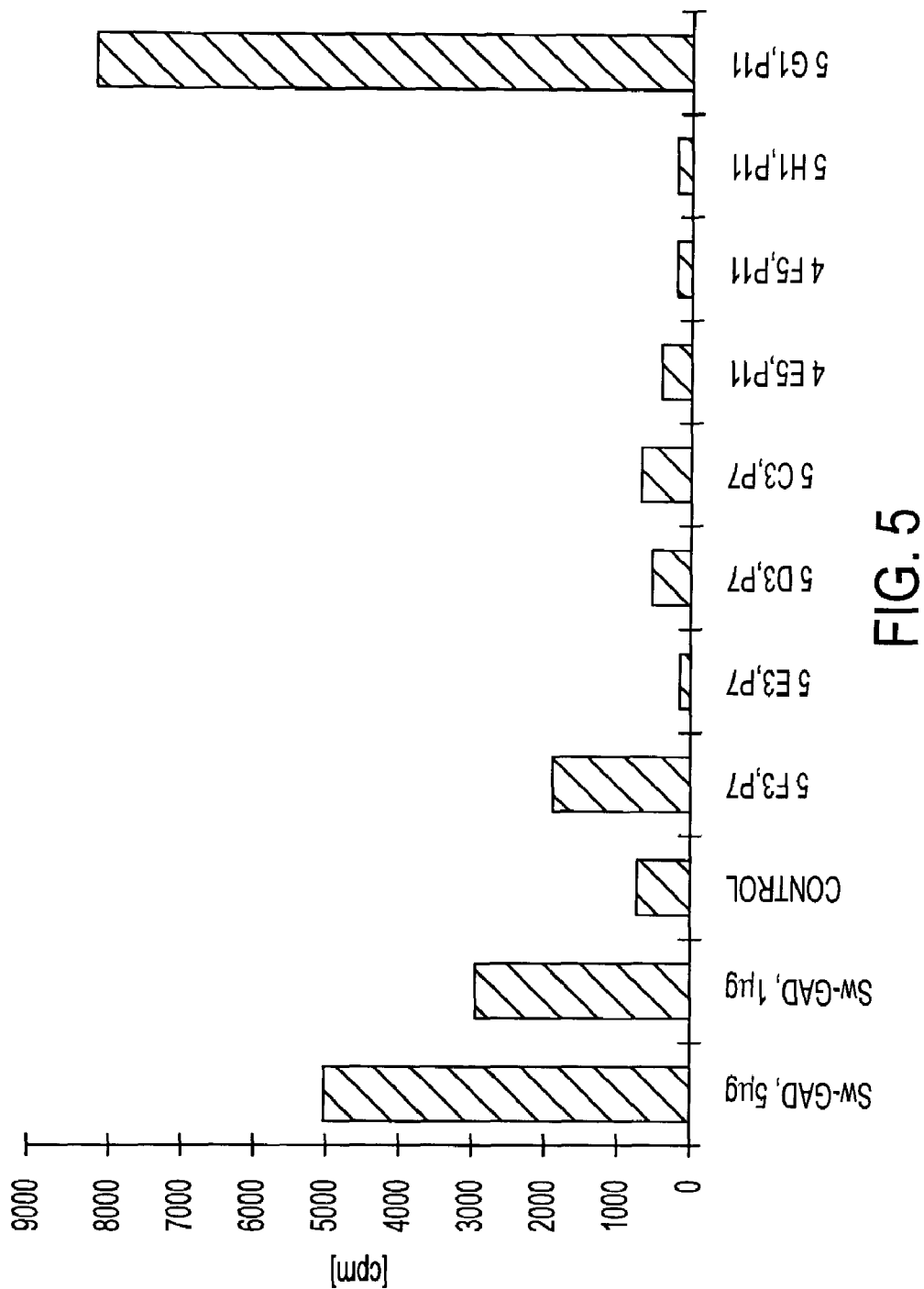

FIG. 3 shows the result of a proliferation assay of the T cell line 6/7 with peptide pools FIG. 4 shows the result of a proliferation assay of the T cell line 6/10 with peptide pools FIG. 5 shows the result of a proliferation assay with the T cell line 6/7 with individual peptides from pool 7 and 11

FIG. 6 shows the result of a proliferation assay with the T cell line 6/10 with individual peptides from pool 7 and 11

EXAMPLE 1

Setting Up GAD-Specific T Cell Lines

1. Primary Stimulation

Peripheral blood lymphocytes (PBLs) are isolated from EDTA blood of type I diabetics by Ficoll density gradient centrifugation. The cells are washed twice in RPMI medium and then taken up in a culture medium composed of RPMI 1640, 5% human serum, 2 mM glutamine and 100 U/ml penicillin and 100 µg/ml streptomycin. 100 µl cell suspension, corresponding to 100 000 cells, are sown into each well of a 96 well round-bottom plate. Afterwards porcine GAD (SW-GAD) is added at a final concentration of 2.5 µg/ml. The cells are incubated for 3–4 days in an incubator at 37° C./7% $CO_2$. After this time period, 100 µl IL-2 (30 U/ml) is added. After a further 3–4 days, 100 µl is aspirated from all culture mixtures and again 100 µl IL-2 (30 U/ml) is added. This is repeated every 3–4 days.

2. Restimulation

The first restimulation is carried out on the 14th day after the beginning of the primary stimulation. For this, in comparison to the primary stimulation, double the number of autologous PBLs is isolated by means of Ficoll and adjusted in culture medium to a cell concentration of $2 \times 10^6$/ml. One half of these stimulator cells is incubated for 2 hours/37° C./7% $CO_2$ with the antigen SW-GAD (final concentration 5 µg/ml) (antigen pulse). The other half is incubated under the same conditions without antigen and only with culture medium. Subsequently all stimulator cells are irradiated with 4000 rad. The stimulator cells are then distributed (100 000 cells/well) in 96 well round-bottom plates in such a way that a well with stimulator cells containing antigen is always adjacent to a well with stimulator cells without antigen.

Subsequently the T cells are prepared from the primary stimulation preparations. For this the supernatants from the primary stimulation preparations are aspirated and the cells in the plates are washed twice with 100 µl washing medium each time (Dulbecco's Modified Eagle Medium=DMEM). Between these the cells are centrifuged in the plates at 400 g. Subsequently the cells are taken up in 100 µl culture medium in each case and 50 µl thereof is distributed in each case into two adjacent wells of the restimulation plate. In this manner the T cells are incubated in one well with antigen and in the adjacent well without antigen it is possible to monitor the antigen specificity of the restimulation.

From the 2nd or 3rd day after the start of the restimulation it is possible to assess the proliferation by microscopy. In this process only those microculture pairs are regarded as being relevant in which proliferation only occurs in the well in which antigen is present. From the 4th day 100 µl IL-2 (30 U/ml) is in turn added to each culture well. Up to the 14th day ca. 50% of the culture medium is exchanged for IL-2 (30 U/ml) every 3–4 days.

When the growth is good the cultures are divided among several 96 well plates. In the later restimulation it is also possible to distribute them into larger wells. A renewed restimulation is carried out by the aforementioned method every two weeks. From the 3rd restimulation onwards the specificity of the microcultures is determined in a proliferation test.

3. Proliferation Test with SW-GAD

All tests are carried out in at least duplicate preparations.

a) Stimulator Cells:

Autologous PBLs or PBLs of a normal donor which are identical with regard to the HLA class II antigens are used as stimulator cells. The PBLs are pre-incubated with antigen as described in paragraph 2, irradiated with 4000 rad and distributed in 96 well plates (100 000 cells/well).

b) T Cells

The T cells which were used are derived always from the final stage of a restimulation period. They are washed three times free of antigen and IL-2 using DMEM and divided into 6000 cells/96 wells. The T cell lines 6/7 and 6/10 isolated in this manner were deposited at the DSM according to the regulations of the Budapest Treaty under the numbers DSM ACC2172 and DSM ACC2173.

In addition to the incubations with SW-GAD, controls are incubated without GAD.

After 3–4 days at 37° C./7% $CO_2$, 1 µCi $^3$H-thymidine is added and incubated for a further 16–20 hours. Afterwards the cells are transferred onto a glass fibre filter by means of a cell harvester instrument and the incorporated radioactivity is determined in a β counter.

Table 1 shows a typical result of a proliferation test with SW-GAD

TABLE 1

Results of a proliferation test of T cell lines 6/7 and 6/10 with SW-GAD

| Cell line | Control without antigen | cpm SW-GAD |
|---|---|---|
| 6/7 | 129 | 9373 |
| 6/10 | 117 | 5222 |

4. Proliferation Test with Peptides that are Derived from the H-GAD Sequence

T cell lines that had been expanded by means of at least 4 restimulation cycles and which reacted with SW-GAD in the proliferation test were additionally tested with overlapping peptides of H-GAD. The object of these experiments is to define the epitopes of H-GAD that are recognized by the T cells. For this, overlapping 20 mer peptides of H-GAD are firstly synthesized (overlapping region 10 amino acids, total of 59 different peptides).

In each case 4–5 of these peptides are combined to form a pool and added to the stimulator cells at a final concentration of 18 µg/ml in each case (the stimulator cells are prepared as described in section 3a). The further treatment of these stimulator cells is carried out as described in section 3a.

Subsequently 6000–20,000 T cells are added per microculture well. The further procedure is analogous to that described in section 3b.

FIGS. 3 and 4 show the results of a proliferation assay of the T cell lines 6/7 and 6/10 using peptide pools of the human GAD 65 kd. Both T cell lines proliferate strongly with peptides from pool 11. A smaller but significant proliferation is also observed with pool 7.

FIGS. 5 and 6 show the results of the proliferation assay of the T cell lines 6/7 and 6/10 with 10 µg/ml individual peptides from pools 7 and 11. Both cell lines show a significant proliferation with peptide 5G1 (corresponding to amino acids 266–285 of human GAD 65) and a smaller but significant proliferation with peptide 5F3 (corresponding to amino acids 306–325 of human GAD 65).

EXAMPLE 2

Method for the Isolation and Determination of an Antigen-Specific T Cell Subpopulation Since antigen-specific T lymphocytes and particularly those directed towards autoantigens occur in peripheral blood in a very low number (expected frequency $10^{-5}$–$10^{-6}$) the obvious thing is to firstly concentrate the in vivo pre-activated T cells by means of a selection step. This can be achieved by two methods:

1. Expansion of In Vivo Pre-Activated T Cells by Incubation with IL-2

For this PBLs are isolated by means of Ficoll density gradient centrifugation and adjusted in cell culture medium containing IL-2 (RPMI 1640/5% human serum/30 U/ml IL-2) to $2 \times 10^6$ cells/ml. 200 µl aliquots of the cells are distributed among 48 well plates and incubated for 7 days. After 4 days IL-2 is additionally added once again. Since pre-activated T cells express the high affinity IL-2 receptor, the in vivo pre-activated T cells proliferate selectively during this stimulation period and accumulate in the primary culture. After the conclusion of the stimulation period, the cells are washed in the individual wells, counted and used in a proliferation test.

2. Concentration of In Vivo Pre-Activated T Cells by Immunomagnetic Separation

For this the Ficoll-isolated PBLs are incubated with monoclonal antibodies against the high affinity IL-2 receptor ($7 \times 10^6$ PBLs/ml; 10 µg/ml anti IL-2 receptor antibody (Boehringer Mannheim); 30 min at 4° C.). Subsequently the cell suspension is washed twice with ice-cold RPMI/10% human serum (HS) (400 g/10 min) and then the suspension is adjusted to a cell density of $1–3 \times 10^7$/ml. Dynabeads M-280 from the Dynal company that are coupled to sheep anti-mouse antibodies are added to this (ratio of Dynabeads to target cells ca. 10–15). The suspension is moved very slowly at 4° C. on a roller. Afterwards the suspension is diluted ten-fold with RPMI/10% HS and placed for 1–2 minutes in the previously cooled magnetic particle concentrator (MPC). After the rosetted T cells carrying the IL-2 receptor have been immobilized by the magnet, the supernatant is aspirated, the incubation vessel is removed from the MPC and the remaining cells are resuspended in RPMI/10% HS. The separation of the target cells is carried out once again in MPC. This washing step is repeated once again. Subsequently the separated cells are resuspended in culture medium and the cell number is adjusted to $1 \times 10^7$/ml. The magnetobeads are removed by known methods by means of detacher antibodies.

The pre-activated cells concentrated by means of the processes according to 2.1 or 2.2 are subsequently tested for reactivity against the auto-antigen peptides or against a peptide/MHC complex. There are also several methods for this:

3. Proliferation Test with Irradiated Stimulator Cells and Peptides as Antigens

Firstly autologous stimulator cells are prepared from Ficoll-isolated PBLs. The stimulator cells are adjusted to a concentration of $10^6$ cells/ml in cell culture medium and incubated with the peptides (final concentration 10 µg/ml) for 2 hours/37° C./7% $CO_2$. Afterwards the stimulator cells are irradiated with 4000 rad and subsequently distributed in a 96-well round-bottom plate using a cell number of 100 000 cells/well.

100 000 of the in vivo pre-activated T cells obtained from 2.1 or 2.2 are added to this in each case and incubated for 4 days/37° C./7% $CO_2$. Then half of the preparation volume is exchanged for IL-2 (30 U/ml). This is repeated once again after a further 4 days.

On the 12th day after the start of the microculture, the actual proliferation test is carried out. For this the microcultures are firstly washed twice with DMEM in order to remove antigen and IL-2. Each culture is divided into 4 aliquots and incubated (37° C./7% $CO_2$) for 3 days in duplicates in the presence of 100 000 autologous irradiated PBLs, in each case with or without a peptide pulse. After this period $^3$H-thymidine is added and the incorporated radioactivity is determined after a further 16–20 hours.

4. Direct Detection of Autoantigen-Reactive T Cells by Labelling by Means of an Oligomerized Peptide/HLA Complex The in vivo pre-activated T cells concentrated according to method 2.2 are used for this. The cells are adjusted in RPMI/10% HS to a concentration of $10^6$/ml and incubated at 4° C. for 30 minutes with the oligomerized HLA-peptide complex provided with a fluorescent label. Subsequently the cells are washed twice with ice-cold cell culture medium. The analysis of the fluorecent-labelled cell population is carried out in a flow cytometer.

EXAMPLE 3

Identification of MHC Molecules that Present a Defined Autoreactive Peptide

The peptides are firstly labelled with $^{125}$I for this e.g. according to the method of Bolton and Hunter (Bolton, A. E. and Hunter, W. M., Biochem. J. 133 (1993), 529–531). Then 2–5×$10^6$ PBLs of the donor having the MHC-type to be examined are incubated for 4 hours at 37° C. in cell culture medium containing $^{125}$I-labelled peptides (2–10 µM). After washing the cells, these are lysed in a lysis buffer composed of 0.5% NP 40; 0.5% Mega9; 150 mM NaCl; 5 mM EDTA; 50 mM Tris pH 7.5; 2 mM phenylmethylsulfonyl fluoride). The MHC molecules are immunoprecipitated from the mixture by framework-specific monoclonal antibodies (e.g. with the monoclonal antibody L243 (ATCC HB 55) in the case of HLA-DR) bound to protein A-Sepharose and the radioactivity bound to the protein A-Sepharose is determined in a gamma counter.

EXAMPLE 4

Determination of the Subtype of MHC Molecules that Present Autoreactive Peptides to the T Cell Lines 6/7 (DSM ACC2172) and 6/10 (DSM ACC2173)

The experimental procedure is analogous to example 1.3. However, autologous PBLs were not used as antigen-presenting cells, but instead PBLs from heterologous donors which do not completely correspond to the MHC molecules of the donor from which the T cell lines were also developed but only with regard to defined MHC alleles. The proliferation tests were carried out using the autoantigenic peptides 5G1 (corresponding to amino acids 266–285 of human GAD65) and 5F3 (corresponding to amino acids 306–325 of human GAD65).

Table 3 shows the result of such a test mixture. The T cell lines 6/7 and 6/10 proliferate with both peptides in the presence of the DR B1 allele 0401. Variation of the DQ A1 or DQ B1 allele does not have an influence on the stimulatability of the T cell lines. The T cell line 6/7 recognizes the peptide 5G1 additionally in association with the alleles DR B1 0101 or/and 1601.

T cell proliferation after stimulation with the peptides 5G1 and 5F3 using PBLs with various haplotypes as antigen-presenting cells

TABLE 3

| Donor | Haplotype of APC | | | Identicalness of the alleles with the alleles of the donor of the TCL | TCL 6/7 | | TCL 6/10 | |
|-------|------|------|------|---|---|---|---|---|
| | DR B1* | DQ A1* | DQ B1* | | +peptide | SI | +peptide | SI |
| A.K.  | 0301 | 0501 | 0201 | DR: 2 alleles ident. | 5G1 | 55.0 | 5G1 | 6.0 |
|       | 0401 | 0301 | 0302 | DQ: 4 alleles ident. | 5F3 | 3.8  | 5F3 | 3.8 |
| G.H.  | 0301 | 0501 | 0201 | DR: 1 allel ident. | 5G1 | 0.9  | 5G1 | 1.5 |
|       |      |      |      | 1 allel not ident. | 5F3 | 0.6  | 5F3 | 1.5 |
|       | 0404 | 0301 | 0302 | DQ: 4 allels ident. | | | | |
| G.E.  | 1302 | 0102 | 0604 | DR: 1 allel ident. | 5G1 | 67.8 | 5G1 | 22.6 |
|       |      |      |      | 1 allel not ident. | 5F3 | 7.0  | 5F3 | 6.5 |
|       | 0401 | 0301 | 0302 | DQ: 2 allels ident. | | | | |
|       |      |      |      | 2 allels not ident. | | | | |
| 19    | 0301 | 0501 | 0301 | DR: 2 allels ident. | 5G1 | 45.7 | 5G1 | 8.5 |
|       | 0401 | 0201 | 0301 | DQ: 1 allel ident. | 5F3 | 3.1  | 5F3 | 2.8 |
|       |      |      |      | 3 allels not ident. | | | | |
| D.J.  | 0101 | 0101 | 0501 | DR: 2 allels not ident. | 5G1 | 28.6 | 5G1 | 2.2 |
|       | 1601 | 0102 | 0502 | DQ: 4.allels not ident. | 5F3 | 1.2  | 5F3 | 1.4 |

TCL = T cell line
APC = antigen-presenting cells
SI = stimulation index: cpm in the presence of peptide divided by cpm without peptide.

EXAMPLE 5

Proliferation Test with Variants of the Peptide 5G1 Using the T Cell Line 6/10

In order to elucidate the core structure of the stimulating peptide 5G1, proliferation tests were carried out with various variants of this peptide using the T cell line 6/10 (see Table 4).

A test with a first series of 20 mer variants is intended to ascertain whether amino acids which border on the 5G1 structure at the C- or N-terminus play a role in the recognition by the T cell line 6/10. As the stimulation indices show, a shift of the 20 mer peptide in the direction of the C-terminus does not lead to an increase in the proliferation activity. A 6 amino acid shift towards the N-terminus leads to a loss in stimulation capacity.

A test with a second series of peptide variants examines the influence of a shortening at the C-terminus. This series of experiments shows that the C-terminal amino acid residues histidine (H) and phenylalanine (F) are important for the stimulation capacity.

The object of a test with a third series of peptide variants was to define the N-terminus of the minimum stimulation-active peptide. If the amino acids leucine (L) and proline (P) are removed from a 18 mer with an intact C-terminus, this leads to a strong decrease of the stimulation index. The N-terminus is thus defined by L and P. If the C-terminus is shortened further by H and F this also leads to a loss of stimulation activity.

Thus in the case of the T cell line 6/10 the minimum peptide that can still stimulate is a 14 mer having the sequence LPRLIAFTSEHSHF. (SEQ ID NO:4)

TABLE 4

Reaction of TCL 6/10 with variants of the peptide 5G1 in order to identify the minimum peptide structure which still has stimulation activity

| Peptide variants of 5G1 | | Stimulation index |
|---|---|---|
| 5G1 | GMAALPRLIAFTSEHSHFSL (SEQ ID NO:5) | 5.4 |
| | ALPRLIAFTSEHSHFSLKKG (SEQ ID NO:6) | 3.0 |
| | RLIAFTSEHSHFSLKKGAAA (SEQ ID NO:7) | 3.2 |
| | PEVKEKGMAALPRLIAFTSE (SEQ ID NO:8) | 0.6 |
| | AALPRLIAFTSEHSHFSL (SEQ ID NO:9) | 4.5 |
| | AALPRLIAFTSEHSHF (SEQ ID NO:10) | 2.9 |
| | AALPRLIAFTSEHS (SEQ ID NO:11) | 0.7 |
| | AALPRLIAFTSE (SEQ ID NO:12) | 0.6 |
| | GMAALPRLIAFTSE (SEQ ID NO:13) | 0.8 |
| | GMAALPRLIAFT (SEQ ID NO:14) | 1.0 |
| | LPRLIAFTSEHSHFSLKK (SEQ ID NO:15) | 3.2 |
| | RLIAFTSEHSHFSL (SEQ ID NO:16) | 1.4 |
| | LPRLIAFTSEHSHF (SEQ ID NO:17) | 4.6 |
| | LPRLIAFTSEHS (SEQ ID NO:18) | 0.4 |

The invention claimed is:

1. An isolated complex comprising:
a peptide of glutamic acid decarboxylase which is selected from the group consisting of SEQ ID NO: 2, 3, 19–39 and a fragment thereof that has at least 6 contiguous amino acids of SEQ ID NO: 2, 3 or 19–39, which is bound to an allele of MHC Class II molecules DR3 or DR4 selected from the group consisting of DR B1 0301, DR B1 0401, DR B1 0402, DR B1 0404 and peptide-binding fragments thereof.

2. The complex of claim 1, wherein the MHC class II molecules have the subtype DR B1 301 or DR B1 0401.

3. The complex of claim 1, wherein the MHC class II molecules are recombinant MHC class II molecules.

4. The complex of claim 1, wherein the peptide is bound to a soluble MHC class II DR3 or DR4 molecule selected from the group consisting of DR B1 0301, DR B1 0401, DR B1 0402, DR B1 0404 and peptide-binding fragments thereof.

5. The complex of claim 1, wherein the complex carries a marker group.

6. The complex of claim 1, wherein the peptide carries a marker group.

7. A composition, comprising a complex as claimed in claim 1, in combination with a pharmaceutically acceptable carrier.

8. The pharmaceutical composition of claim 7, further comprising an accessory stimulating component, wherein the accessory stimulating component is a cytokine, surface antigen B7, or both.

9. An isolated complex comprising:
a peptide of glutamic acid decarboxylase which is selected from the group consisting of SEQ ID NO: 2, 3, 19–39 and a fragment thereof that has at least 12 contiguous amino acids of SEQ ID NO: 2, 3 or 19–39, which is bound to an allele of MHC Class II molecules DR3 or DR4 selected from the group consisting of DR B1 0301, DR B1 0401, DR B1 0402, DR B1 0404 and peptide-binding fragments thereof.

10. An isolated complex comprising:
a peptide of glutamic acid decarboxylase which is selected from the group consisting of SEQ ID NO: 2, 3, 19–39 and a fragment thereof that has at least 6 contiguous amino acids of SEQ ID NO: 2, 3 or 19–39, wherein a reactive backbone and/or amino acid side group of said peptide has been derivatized by a chemical reaction,
which is bound to an allele of MHC Class II molecules DR3 or DR4 selected from the group consisting of DR B1 0301, DR B1 0401, DR B1 0402, DR B1 0404 and peptide-binding fragments thereof.

11. The complex of claim 10, wherein the peptide is bound to a soluble MHC class II DR3 or DR4 molecule selected from the group consisting of DR B1 0301, DR B1 0401, DR B1 0402, DR B1 0404 and peptide-binding fragments thereof.

12. The complex of claim 10, wherein the peptide carries a marker group.

13. An isolated complex comprising:
a peptide of glutamic acid decarboxylase which is selected from the group consisting of SEQ ID NO: 2, 3, 19–39 and a fragment thereof that has at least 12 contiguous amino acids of SEQ ID NO: 2, 3 or 19–39, wherein a reactive backbone and/or amino acid side group of said peptide has been derivatized by a chemical reaction,
which is bound to an allele of MHC Class II molecules DR3 or DR4 selected from the group consisting of DR B1 0301, DR B1 0401, DR B1 0402, DR B1 0404 and peptide-binding fragments thereof.

14. An isolated complex comprising:
a peptide of glutamic acid decarboxylase which is selected from the group consisting of SEQ ID NO: 2, 3, 19–39 and a fragment thereof that has at least 6 contiguous amino acids of SEQ ID NO: 2, 3 or 19–39, wherein at least one amino acid of said peptide is replaced with a homolog of said amino acid selected from the group consisting of 4-hydroxyproline, 5-hydroxylysine, 3-methyl histidine, homoserine, ornithine, β-alanine and 4-aminobutyric acid,
which is bound to an allele of MHC Class II molecules DR3 or DR4 selected from the group consisting of DR B1 0301, DR B1 0401, DR B1 0402, DR B1 0404 and peptide-binding fragments thereof.

15. The complex of claim 14, wherein the peptide is bound to a soluble MHC class II DR3 or DR4 molecule selected from the group consisting of DR B1 0301, DR B1 0401, DR B1 0402, DR B1 0404 and peptide-binding fragments thereof.

16. The complex of claim 14, wherein the peptide carries a marker group.

17. An isolated complex comprising:
a peptide of glutamic acid decarboxylase which is selected from the group consisting of SEQ ID NO: 2, 3, 19–39 and a fragment thereof that has at least 12 contiguous amino acids of SEQ ID NO: 2, 3 or 19–39, wherein at least one amino acid of said peptide is replaced with a homolog of said amino acid selected from the group consisting of 4-hydroxyproline, 5-hydroxylysine, 3-methyl histidine, homoserine, ornithine, β-alanine and 4-aminobutyric acid,
which is bound to an allele of MHC Class II molecules DR3 or DR4 selected from the group consisting of DR B1 0301, DR B1 0401, DR B1 0402, DR B1 0404 and peptide-binding fragments thereof.

* * * * *

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1
       (D) OTHER INFORMATION: /note= "Xaa in position 1 is an
           optional sequence selected from 1 to 10 amino acids."

(ix) FEATURE:
       (A) NAME/KEY: Peptide
       (B) LOCATION: 6
       (D) OTHER INFORMATION: /note= "Xaa in position 6 is Thr or
           Glu."

(ix) FEATURE:
        (A) NAME/KEY: Peptide
        (B) LOCATION: 8
        (D) OTHER INFORMATION: /note= "Xaa in position 8 is
            an optional sequence selected from 1 to 8 amino acids."

(xi) SEQUENCE DESCRIPTION: SEQ ID NO:1:

Xaa Pro Glu Val Lys Xaa Lys Xaa
1               5

(2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Gly Met Ala Ala Leu Pro Arg Leu Ile Ala Phe Thr Ser Glu His Ser
1               5                   10                  15

His Phe Ser Leu Lys Lys Gly Ala Ala
                20                  25

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Glu Arg Gly Lys Met Ile Pro Ser Asp Leu Glu Arg Arg Ile Leu Glu
1               5                   10                  15

Ala Lys Gln Lys
                20

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Leu Pro Arg Leu Ile Ala Phe Thr Ser Glu His Ser His Phe
1               5                   10

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Gly Met Ala Ala Leu Pro Arg Leu Ile Ala Phe Thr Ser Glu His Ser
1               5                   10                  15

His Phe Ser Leu
            20

(2) INFORMATION FOR SEQ ID NO:6:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Ala Leu Pro Arg Leu Ile Ala Phe Thr Ser Glu His Ser His Phe Ser
1               5                   10                  15

Leu Lys Lys Gly
            20

(2) INFORMATION FOR SEQ ID NO:7:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Arg Leu Ile Ala Phe Thr Ser Glu His Ser His Phe Ser Leu Lys Lys
1               5                   10                  15

Gly Ala Ala Ala
            20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Pro Glu Val Lys Glu Lys Gly Met Ala Ala Leu Pro Arg Leu Ile Ala
1               5                   10                  15

Phe Thr Ser Glu
            20

(2) INFORMATION FOR SEQ ID NO:9:

(i) SEQUENCE CHARACTERISTICS:
            (A) LENGTH: 18 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Ala Ala Leu Pro Arg Leu Ile Ala Phe Thr Ser Glu His Ser His Phe
1               5                   10                  15

Ser Leu (2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Ala Ala Leu Pro Arg Leu Ile Ala Phe Thr Ser Glu His Ser His Phe
1               5                   10                  15

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Ala Ala Leu Pro Arg Leu Ile Ala Phe Thr Ser Glu His Ser
1               5                   10

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Ala Ala Leu Pro Arg Leu Ile Ala Phe Thr Ser Glu
1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Gly Met Ala Ala Leu Pro Arg Leu Ile Ala Phe Thr Ser Glu
1               5                   10

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS:
        (D) TOPOLOGY: linear

```
      (ii) MOLECULE TYPE: peptide (xi) SEQUENCE DESCRIPTION: SEQ ID NO:14:

Gly Met Ala Ala Leu Pro Arg Leu Ile Ala Phe Thr
1               5                  10

(2) INFORMATION FOR SEQ ID NO:15:

(i) SEQUENCE CHARACTERISTICS:
          (A) LENGTH: 18 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:15:

Leu Pro Arg Leu Ile Ala Phe Thr Ser Glu His Ser His Phe Ser Leu
1               5                  10                  15

Lys Lys (2) INFORMATION FOR SEQ ID NO:16:

(i) SEQUENCE CHARACTERISTICS:
          (A) LENGTH: 14 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:16:

Arg Leu Ile Ala Phe Thr Ser Glu His Ser His Phe Ser Leu
1               5                  10

(2) INFORMATION FOR SEQ ID NO:17:

(i) SEQUENCE CHARACTERISTICS:
          (A) LENGTH: 14 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:17:

Leu Pro Arg Leu Ile Ala Phe Thr Ser Glu His Ser His Phe
1               5                  10

(2) INFORMATION FOR SEQ ID NO:18:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:18:

Leu Pro Arg Leu Ile Ala Phe Thr Ser Glu His Ser
1               5                  10
```

(2) INFORMATION FOR SEQ ID NO:19:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Ile Leu Ile Lys Cys Asp Glu Arg Gly Lys Met Ile Pro Ser
1               5                   10
```

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Leu Gly Ile Gly Thr Asp Ser Val Ile Leu Ile Lys Cys Asp
1               5                   10
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Leu Ala Phe Leu Gln Asp Val Met Asn Ile Leu Leu Gln Tyr
1               5                   10
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Tyr Asp Leu Ser Tyr Asp Thr Gly Asp Lys Ala Leu Gln Cys
1               5                   10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

```
Val Ser Tyr Gln Pro Leu Gly Asp Lys Val Asn Phe Phe Arg
1               5                   10
```

```
(2) INFORMATION FOR SEQ ID NO:24:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Leu Ala Ala Asp Trp Leu Thr Ser Thr Ala Asn Thr Asn Met
1               5                   10

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE:  peptide (xi) SEQUENCE DESCRIPTION: SEQ ID NO:25:

Leu Leu Tyr Gly Asp Ala Glu Lys Pro Ala Glu Ser Gly Gly
1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Val Asn Tyr Ala Phe Leu His Ala Thr Asp Leu Leu Pro Ala
1               5                   10

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Leu Leu Gln Tyr Val Val Lys Ser Phe Asp Arg Ser Thr Lys
1               5                   10

(2) INFORMATION FOR SEQ ID NO:28:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Phe Thr Tyr Glu Ile Ala Pro Val Phe Val Leu Leu Glu Tyr
1               5                   10
```

(2) INFORMATION FOR SEQ ID NO:29:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Leu Glu Tyr Val Thr Leu Lys Lys Met Arg Glu Ile Ile Gly
1               5                  10
```

(2) INFORMATION FOR SEQ ID NO:30:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Asn Met Tyr Ala Met Met Ile Ala Arg Phe Lys Met Phe Pro
1               5                  10
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Lys Ile Trp Met His Val Asp Ala Ala Trp Gly Gly Gly Leu
1               5                  10
```

(2) INFORMATION FOR SEQ ID NO:32:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Trp Gly Gly Gly Leu Leu Met Ser Arg Lys His Lys Trp Lys
1               5                  10
```

(2) INFORMATION FOR SEQ ID NO:33:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Glu Gly Tyr Glu Met Val Phe Asp Gly Lys Pro Gln His Thr
1               5                  10
```

-continued (2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Arg Tyr Phe Asn Gln Leu Ser Thr Gly Leu Asp Met Val Gly
1               5                   10
```

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Trp Leu Thr Ser Thr Ala Asn Thr Asn Met Phe Thr Tyr Glu
1               5                   10
```

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Thr Ala Asn Thr Asn Met Phe Thr Tyr Glu Ile Ala Pro Val
1               5                   10
```

(2) INFORMATION FOR SEQ ID NO:37:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Leu Val Ser Ala Thr Ala Gly Thr Thr Val Tyr Gly Ala Phe
1               5                   10
```

(2) INFORMATION FOR SEQ ID NO:38:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Tyr Ile Pro Pro Ser Leu Arg Thr Leu Glu Asp Asn Glu Glu
1               5                   10
```

-continued (2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Val Ile Ser Asn Pro Ala Ala Thr His Gln Asp Ile Asp Phe
1         5                  10